US00PP29699P3

(12) United States Plant Patent
Carruth

(10) Patent No.: US PP29,699 P3
(45) Date of Patent: Sep. 25, 2018

(54) SHRUB ROSE PLANT NAMED 'WEKMORIDAHOR'

(50) Latin Name: *Rosa hybrida*
Varietal Denomination: WEKmoridahor

(71) Applicant: Early Morning LLC, Lawrenceburg, IN (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 0 days.

(21) Appl. No.: 15/530,011

(22) Filed: Nov. 18, 2016

(65) Prior Publication Data

US 2018/0146582 P1 May 24, 2018

(51) Int. Cl.
*A01H 5/02* (2018.01)

(52) U.S. Cl.
USPC ..... Plt./108
CPC ..... *A01H 5/0222* (2013.01)

(58) Field of Classification Search
USPC ..... Plt./101, 102, 108
See application file for complete search history.

(56) References Cited

U.S. PATENT DOCUMENTS

PP16,572 P3 5/2006 Carruth
PP18,552 P3 3/2008 Carruth

OTHER PUBLICATIONS

Weeks Roses, 2017 Catalog, 92 pages.

*Primary Examiner* — Susan McCormick Ewoldt
*Assistant Examiner* — Karen M Redden
(74) *Attorney, Agent, or Firm* — McKee, Voorhees & Sease, PLC

(57) ABSTRACT

A new variety of Shrub rose suitable for garden decoration, having flowers of dark red coloration.

1 Drawing Sheet

Classification: The present invention relates to a new *Rosa hybrida* plant.

Variety denomination: The new plant has the varietal denomination 'WEKmoridahor'.

BACKGROUND OF THE INVENTION

This invention relates to a new and distinct variety of Shrub Rose. It has as its seed parent the variety known as 'WEKblunez' (U.S. Plant Pat. No. 16,572) and as its pollen parent the variety known as 'WEKcisbako' (U.S. Plant Pat. No. 18,552).

SUMMARY OF THE INVENTION

Among the features which distinguish the new variety from other presently available and commercial rose cultivars known to the inventor are the following combinations of characteristics: its high degree of resistance to black spot, powdery mildew, downy mildew and rust, its excellent color stability throughout the life of the flower and its abundant bloom. The plant has a moderately spreading bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmoridahor' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKblunez' by the following combination of characteristics: whereas 'WEKmoridahor' bears semi-double flowers (about 6 to 10 petals) of dark red coloration, 'WEKblunez' bears very double flowers of orchid pink coloration with significantly heavier petalage (about 28 to 52 petals). The new variety bears medium sized flowers (about 7.0 to about 10.1 cm. in diameter), whereas the seed parent bears significantly larger flowers (about 10.0 to about 12.2 cm. in diameter).

The new variety may be distinguished from its pollen parent, 'WEKcisbako' by the following combination of characteristics: whereas 'WEKmoridahor' bears semi-double flowers (about 6 to 10 petals) of dark red coloration, 'WEKcisbako' bears single flowers of flame red coloration with significantly lesser petalage (about 5 petals). The new variety has a moderately spreading bushy medium height growing habit (about 110 to about 140 cm. in height), whereas the pollen parent has a bushy moderately spreading significantly shorter growing habit (about 90 to about 112 cm. in height).

COMPARISON WITH THE CLOSEST COMMERCIALLY AVAILABLE CULTIVAR

The closest commercially available cultivar to the new variety is the pollen parent 'WEKcisbako' (U.S. Plant Pat. No. 18,552).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety sometimes bears its flowers singly, usually in clusters of two to five or more per stem. Flowers may be borne in regular rounded clusters on strong short to medium length stems (about 10 to about 46 cm.). The cluster ranges from about 10.0 to about 15.0 cm. in diameter. Outdoors, the plant blooms abundantly and nearly continuously during the growing season. The flowers have a moderate fruity fragrance.

BUD

The peduncle is about 2.4 to about 4.6 cm. in length, of average caliper (about 0.2 to about 0.4 cm. in diameter), and usually erect. It is moderately rough, with few stipitate glands. Peduncle color is between 146B and 146C often heavily suffused, especially on the side exposed to the sun, with between 187B and 187A.

Before the calyx breaks, the bud is about 1.0 to about 1.4 cm. in diameter at the widest point, about 1.3 to about 1.7 cm. in length, and pointed to somewhat ovoid in shape. The surface of the bud bears between 9 to 14 foliaceous appendages with some stipitate glands, usually with slender entire foliaceous parts extending beyond the tip of the bud about ¼ or more of its length. Bud color is between 137C and 138A often heavily suffused, especially on the side exposed to the sun, with between 187B and 187A.

The sepals are about 1.8 to about 2.8 cm. in length and about 0.6 to about 1.0 cm. in width at the widest point. The outer surface color of the sepal is between 137C and 138A often heavily suffused, especially on the side exposed to the sun, with between 187B and 187A. The outer surface of the sepal is moderately rough and bears between 0 to 6 foliaceous appendages with some stipitate glands. The inner surface color of the sepal is near 146C broadly bordered by near 137B. After the sepals open, the inner surface color is sometimes moderately suffused, especially on the area exposed to the sun, with between 187B and 187A. The inner surface of the sepal is covered with fine wooly tomentum; sepal margins are lined with some stipitate glands and hairs.

The receptacle of the flower is of medium length (about 0.5 to about 0.7 cm.) and average in caliper (about 0.7 to about 0.8 cm. in diameter). The receptacle is rounded in form with a flat top. Its surface is smooth with very few hairs and with somewhat thin fleshy walls. The receptacle color is between 144A and 137C often heavily suffused, especially on the side exposed to the sun, with between 187B and 187A.

As the petals open (after the calyx breaks), the bud is about 1.3 to about 2.2 cm. in diameter at the widest point, about 1.6 to about 3.2 cm. in length, and moderately ovoid in form. The color of the under and upper surfaces of the newly opened petals is between 53A and 60A moderately suffused with between 187A and 187B. At the point where the petal attaches, there is a moderately small zone of near 4C.

BLOOM

When fully open, the bloom ranges from about 7.0 to about 10.1 cm. in diameter. Petalage is semi-double with about 6 to 10 petals and about 0 to 5 petaloids irregularly arranged. When partially open, the bloom form is moderately ovoid to cupped, and the petals are loosely spiraled to cupped to somewhat undulated with petal edges somewhat reflexed outward. When fully open, the bloom form is more cupped, and the petals are loosely cupped to somewhat undulated with petal edges moderately reflexed outward.

PETALS

The substance of the petals is moderately heavy and of medium thickness, with upper surfaces moderately satiny and under surfaces shiny. The petals are about 2.5 to about 4.8 cm. in length and about 2.7 to about 5.1 cm. in width at the widest point. Petal margins are entire.

The outer petals are moderately obovate to somewhat rounded in shape with rounded apices and sometimes notched with one notch.

The inner petals are moderately obovate in shape with rounded apices and sometimes notched with one notch.

Petaloids are about 1.0 to about 3.8 cm. in length and about 0.6 to about 1.8 cm. in width at the widest point. Petaloids are irregularly shaped moderately oblanceolate to somewhat subulate with rounded apices.

NEWLY OPENED FLOWER

The under surface color of the outer, intermediate and inner petals is between 61C and 53B. At the point where the petal attaches, there is a somewhat large zone of near 4D. The upper surface color of the outer, intermediate and inner petals is between 57B and 53B often moderately suffused with between 187B and 187A. At the point where the petal attaches, there is a moderately large zone of between 158B and 158C.

The under and upper surface colors of the petaloids are similar in coloration to the upper and under surfaces of the intermediate and inner petals.

The general tonality of the newly opened flower is between 57B and 53B often moderately suffused with between 187B and 187A.

THREE-DAY-OLD FLOWER

The under surface color of the outer, intermediate and inner petals is between 64C and 53B often lightly suffused with near 67A. At the point where the petal attaches, there is a somewhat large zone of between 155A and 155B. The upper surface color of the outer, intermediate and inner petals is between 61B and 53B often moderately suffused with between 187B and 187A. At the point where the petal attaches, there is a moderately large zone of between 155A and 155B.

The under and upper surface colors of the petaloids are similar in coloration to the upper and under surfaces of the intermediate and inner petals.

The general tonality of the three-day-old flower is between 61B and 53B often moderately suffused with between 187B and 187A.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 115) and are arranged regularly about the pistils; a few are mixed with petaloids. The filaments are of medium length (about 0.6 to about 1.1 cm.) most with anthers. Filaments are between 8A and 5B in color sometimes lightly suffused with near 53B. The anthers are somewhat small for the class and all open approximately at the same time. Anther color when immature is near 22A on the external part and near 11D on the internal part. Anther color at maturity is near 163A on the external part and near 200A on the internal part. Pollen is abundant and between 22B and 23C in color.

FEMALE REPRODUCTIVE ORGANS

Pistils vary in number (average about 40). The styles are moderately even, somewhat long in length (about 0.4 to about 0.7 cm.), moderately heavy in caliper, and moderately loosely bunched. Stigma color is near 16C. Style color is between 149D and 150D usually heavily suffused with between 53A and 53B. Ovaries are usually all enclosed in the calyx. The ovaries are small in size and between 158A and 158B in color.

Hips have not been observed on this variety when grown in Pomona, Calif.

FOLIAGE

The compound leaves are usually comprised of three to seven leaflets and are borne abundantly. The five-leaflet leaves are about 10.9 to about 15.1 cm. in length and about 8.2 to about 12.9 cm. in width at the widest point, leathery to somewhat crisp in texture on both sides, and glossy in finish on the upper side and moderately glossy in finish on the under side. The leaves have a pinnate venation pattern. The terminal leaflets are about 4.6 to about 7.4 cm. in length and about 3.0 to about 4.3 cm. in width at the widest point, shaped moderately oval to somewhat ovate with acute apices and rounded bases. Their margins are usually simply serrate.

The upper surface color of the mature leaf is between 139A and 147A. The under surface color of the mature leaf is between 137C and 148B. The under and upper colors of the leaf veins on the mature leaf are similar in coloration to the upper and under surfaces colors of the mature leaf. The upper surface color of the young leaf is between 137A and 146A, often heavily suffused with between 187B and 187A. The under surface color of the young leaf is between 147B and 138B, often heavily suffused with between 187B and 187A. The under and upper colors of the leaf veins on the young leaf are similar in coloration to the upper and under surfaces colors of the young leaf The rachis is somewhat light to average in caliper and rough. The upper side is shallowly grooved with some hairs and stipitate glands on the edges of the grooves. The under side of the rachis is rough with few stipitate glands and small prickles. The rachis color is near 146C on the under side and near 138A on the upper side, often heavily suffused on the young leaves with between 187B and 187A.

The stipules are about 0.7 to about 1.4 cm. in length and somewhat wide (about 0.4 to about 1.0 cm.) with moderately short straight points that usually turn out at an angle of more than 45 degrees and sometimes recurve toward the stem. The under and upper surface color of the stipule is between 137B and 137A. The upper and under surfaces of the stipules are smooth in texture.

The petiole is somewhat light to average in caliper and rough. The upper side is shallowly grooved with some hairs and stipitate glands on the edges of the grooves. The under side of the petiole is rough with few stipitate glands and small prickles. The petiole is about 0.6 to about 2.1 cm. in length and about 0.1 to about 0.2 cm in width at the widest point. The petiole color is near 146C on the under side and near 138A on the upper side, often heavily suffused on the young leaves with between 187B and 187A.

The plant displays an above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Pomona, Calif. The plant's winter hardiness and drought/heat tolerance are yet to be determined.

GROWTH

The plant has a moderately spreading bushy medium height growing habit (about 110 to about 140 cm. in height and about 120 to about 160 cm. spread at the widest point), with full branching. It displays vigorous growth and the canes are of somewhat heavy caliper for the class (about 1.3 to about 2.3 cm. in diameter at the widest point).

The color of the major stems is between 146A and 146B. The major stems are rough in texture and they bear some large prickles that are about 0.7 to about 1.1 cm. in length. The large prickles are almost straight, angled slightly downward with a moderately short broad oval base; prickle color is between 165C and 164B often moderately suffused with between 201C and 201D. The major stem bears many small prickles of similar shape and coloration.

The color of the branches is between 137C and 138A. The branches are rough in texture and they bear some large prickles which are of similar shape to the large prickles on the major stems. The prickles are about 0.4 to about 0.6 cm. in length. The prickle color is between 146C and 152D sometimes lightly suffused with between 187B and 187C. The branches bear many small prickles of similar shape and coloration.

The color of the new shoots is between 146C and 146B often heavily suffused with between 187B and 187A. The new shoots are rough in texture and they bear few large prickles which are of similar size and shape to the large prickles on the major stems; prickle color is near 146B often moderately suffused with between 187B and 187C. The shoots bear many small prickles of similar shape and coloration.

I claim:

1. A new and distinct Shrub rose plant of the variety substantially as described and illustrated herein.

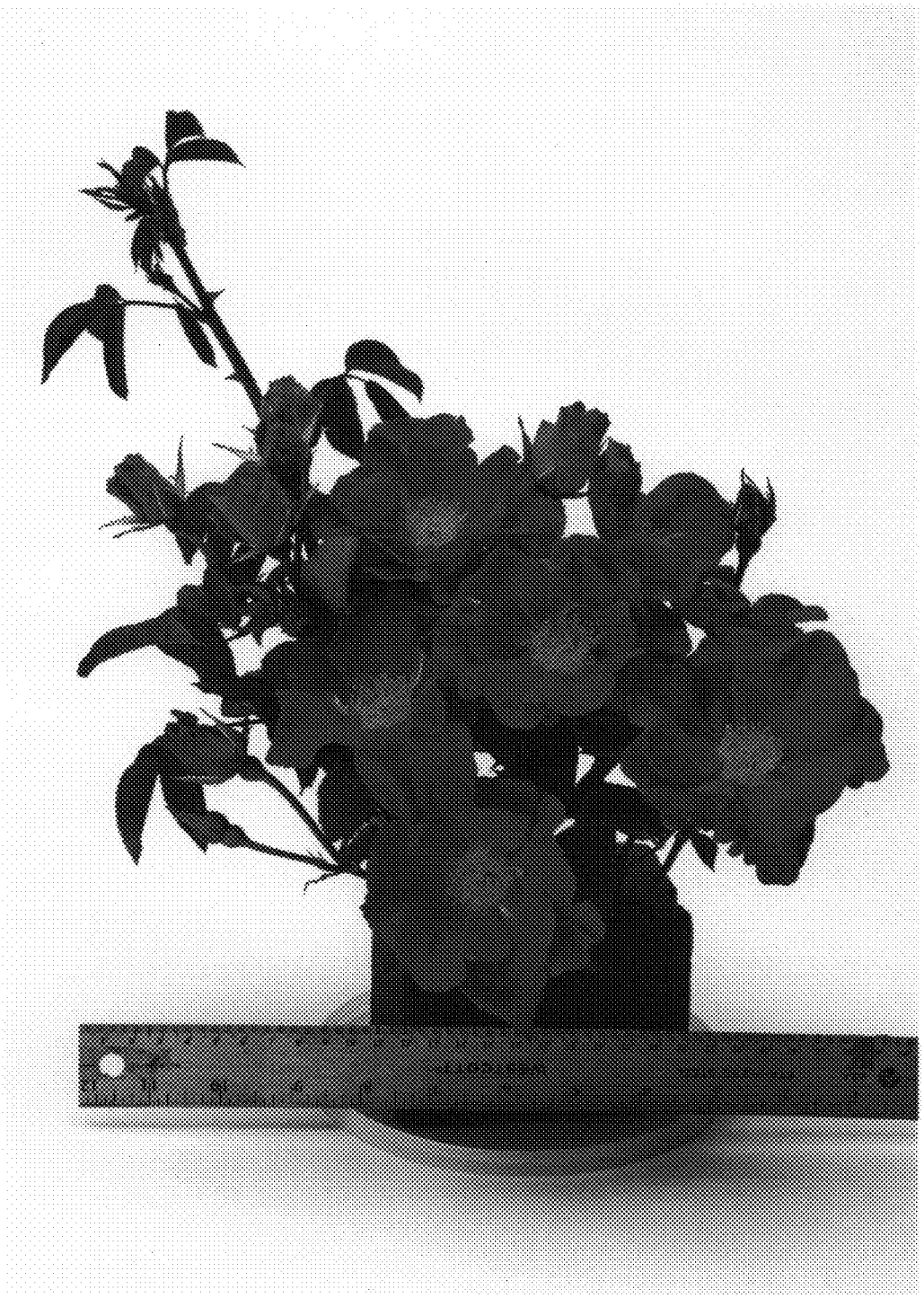

* * * * *